United States Patent [19]

Erhardt et al.

[11] Patent Number: 5,416,097
[45] Date of Patent: May 16, 1995

[54] POTASSIUM CHANNEL ACTIVATORS/OPENERS

[75] Inventors: Paul W. Erhardt, Sylvania, Ohio; Kenneth J. Shaw, San Rafael, Calif.

[73] Assignee: Berlex Laboratories, Inc., Wayne, N.J.

[21] Appl. No.: 63,597

[22] Filed: May 19, 1993

[51] Int. Cl.6 .................. C07D 405/14; A61K 31/40; A61K 31/41; A61K 31/445
[52] U.S. Cl. ....................... 514/320; 514/337; 514/397; 514/414; 514/422; 546/196; 546/269; 548/311.4; 548/454; 548/472
[58] Field of Search ............... 546/201, 196, 290, 301, 546/303, 269; 548/454, 672, 311.4; 514/337, 397, 345, 422, 414, 319, 320

[56] References Cited

U.S. PATENT DOCUMENTS

| | | | |
|---|---|---|---|
| 4,446,113 | 5/1984 | Evans et al. | 546/196 |
| 4,812,459 | 3/1989 | Evans et al. | 514/254 |
| 4,908,378 | 3/1990 | Soll | 514/414 |
| 5,118,694 | 6/1992 | Attwood | 514/337 |
| 5,189,047 | 2/1993 | Hadley | 514/337 |

OTHER PUBLICATIONS

Bergmann et al "Synthesis and antihypertensive Activity of 4-(1,2-dihydro-2oxo-1pyridyl)-2H-1-benzopyrans and Related Compounds, New Potassium Channel Activator" J. Med Chem. 33 492-504 (1990).

Primary Examiner—Celia Chang
Attorney, Agent, or Firm—Elizabeth A. Bellamy; John L. White; John A. Sopp

[57] ABSTRACT

This invention relates to novel potassium channel activators and their acid addition salts. The compounds of the invention as potassium channel activators/openers have therapeutic value in a number of physiological areas such as hypertension, cardiac ischemia, cerebral ischemia, broncho constriction and neurodegenerative diseases. Pharmaceutical compositions are proposed for the compounds which are of the following formulae:

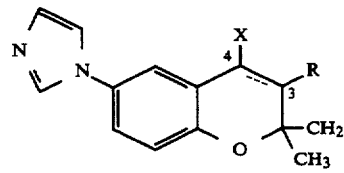

wherein:

R is H or OH;

- - - the dotted line at position 3,4 represents the presence or absence of a double bond.

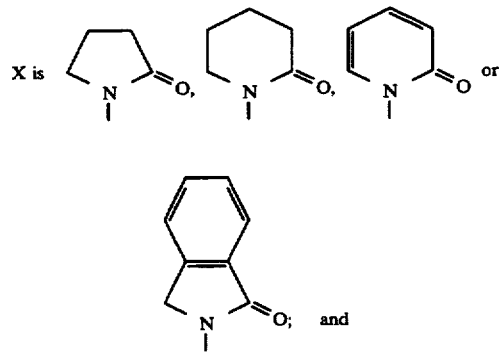

the pharmaceutically acceptable acid addition salts thereof, with the provisos that:

a) R is H when 3,4 is a double bond; and b) R is OH when 3,4 is a single bond.

8 Claims, No Drawings

POTASSIUM CHANNEL ACTIVATORS/OPENERS

SUMMARY OF THE INVENTION

This invention relates to novel potassium channel activators/openers. Thus the compounds of the invention exhibit a variety of pharmacological properties due to enhanced potassium channel flow for which pharmaceutical compositions are proposed.

GENERAL DESCRIPTION OF THE INVENTION COMPOSITION-OF-MATTER ASPECT

In its composition-of-matter aspect, this invention relates to novel potassium channel activators/openers and their acid addition salts.

Compounds encompassed by the invention are of the following Formula I:

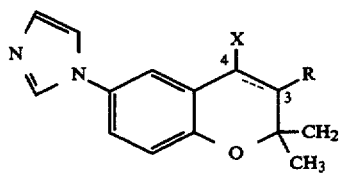

wherein:
R is H or OH;
- - - the dotted line at position 3,4 represents the presence or absence of a double bond;

X is 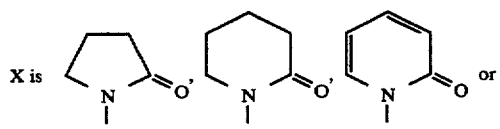 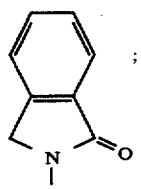 ;

the provisos that:
a) R is H when 3,4 is a double bond; and
b) R is OH when 3,4 is a single bond.

Also contemplated as part of this invention are the pharmaceutically acceptable acid addition salts of the compounds of Formula I. These acid addition salts may be formed with inorganic or organic acids. Illustrative but not restrictive examples of such acids include hydrochloric, hydrobromic, sulfuric, phosphoric, citric, methanesulfonic, 2-hydroxyethanesulfonic, toluenesulfonic, benzenesulfonic, camphorsulfonic, ethanesulfonic, acetic, propanoic, succinic, malic, maleic, adipic, lactic, tartaric and salicylic acids.

It is to be understood that the definition of the compounds of Formula I encompasses all possible stereoisomers and mixtures thereof, which possess the activities discussed herein. In particular, it encompasses the geometrical and optical isomers and the racemic modifications thereof which possess the indicated activities discussed herein.

It is also to be understood that the definition of the compounds of Formula I encompasses all possible polymorphic modifications and other solid state modifications which possess the indicated activities.

Preferred classes of the compounds of Formula I are those wherein:

X is 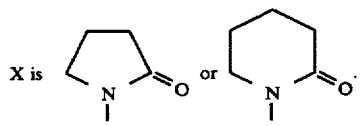

More preferred compounds are those wherein X is as stated above and R is OH and 3,4 - - - is a single bond.

It should be noted that when R is hydroxy and 3,4 is a single bond the hydroxy will always be in a trans configuration to the X substituent.

The compounds which follow are some of those which serve to exemplify, but are not restrictive, to various aspects of the invention described herein.

1) 3,4-dihydro-4-(1,2-dihydro-2-oxopyridyl)-2,2-dimethyl-6-(1H-imidazol-1-yl)-2H-benzo[b]pyran-3-ol, trans.

2) 4-(1,2-dihydro-2-oxopyridyl)-2,2-dimethyl-6-(1H-imidazol-1-yl) -2H-benzo[b]pyran.

3) 3,4-dihydro-2,2-dimethyl-6-(1H-imidazol-1-yl)-4-(1H-isoindol-1-one)-2H-benzo[b]pyran-3-ol, trans.

4) 2,2-dimethyl-6-(1H-imidazol-1-yl)-4-(1H-imidazol-1-one)-2H-benzo[b]pyran.

PROCESS ASPECT

In general, the compounds of the invention may be prepared by various reactants and processes known in the art. Illustrative but not limiting as the reactants and processes utilized for the preparation of the compounds of the invention are the following Schemes A & B.

SCHEME A

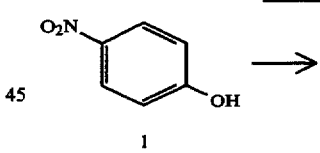

1

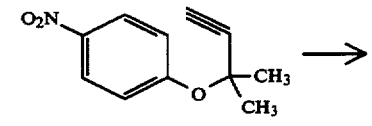

2

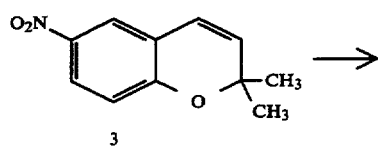

3

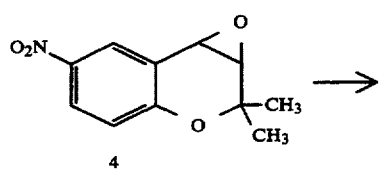

4

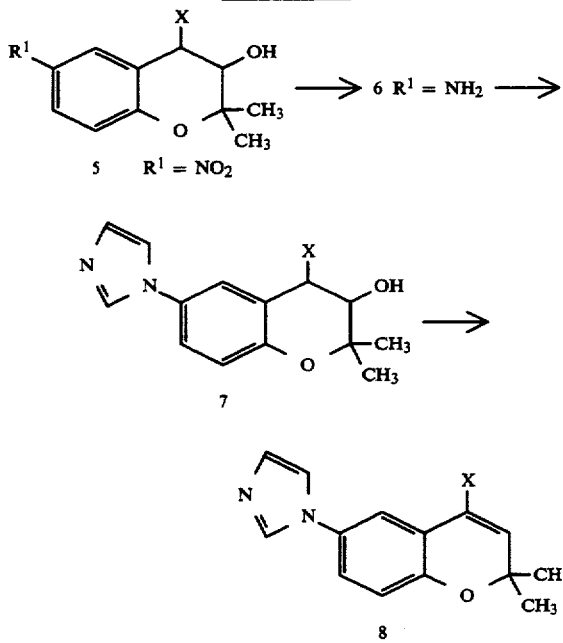

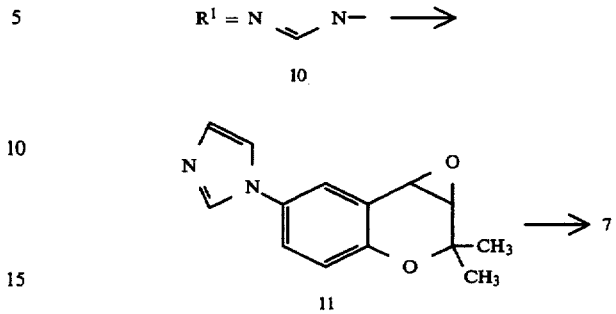

In the above Scheme A the schematic of the conversions are known in the art. In the conversion of compound 1 to compound 3 via compound 2 preparation of compound 2 is best accomplished by phase-transfer catalysis.

It has been usual to convert compound 3 to epoxide compound 4 in a two-step process with isolation of an intermediate bromohydrin. In the above process the conversion takes place as a one-step process wherein compound 3 is combined with 2–7 fold excess of p-nitroperbenzoic acid. After reaction and extraction the resultant epoxide, compound 4 is pure enough to go on in the process. Direct treatment of compound 4 with the desired cyclic amide substituent X in the presence of 1 equivalent of strong base such as sodium hydride is the most straight forward method of converting compound 4 to compound 5. In compound 5 the resulting stereo-chemistry between substituent X and the hydroxyl group is always trans with each intermediate as represented by compound 5 isolated as a racemic mixture.

Reduction of the nitro group fin compound 5 is accomplished by hydrogenation with 10% Pd/C. The resultant compound 6 is converted to the imidazole, compound 7, by reaction with ammonium acetate, acetic acid, glyoxal and formaldehyde. Compositions represented by compound 7 are obtained initially as racemic mixtures of their trans isomers. Conversion of compound 7 to 8 is generally accomplished with sodium hydride.

SCHEME A

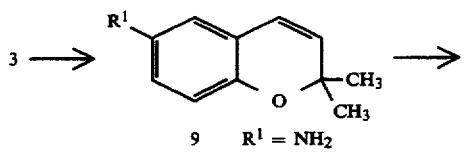

The above Scheme B depicts an alternative process for the formation of the compounds of the invention. As for example, compound 3 is directly converted to the amine and then imidazole using the techniques described above. Similarly compound 10 can be converted to 11 to 7 via analogous techniques as in Scheme A.

Separation of the two enantiomers that are present for each of the four compositions depicted in compound 7 can be accomplished by standard approaches that are known in the chemical arts. Such methods include asymmetric column chromatography and conversion of the enantiomeric relationship to that of a diastereomeric relationship either by formation of synthetic derivatives or stable salt relationships. Reaction of the alcohol function in racemic compound 7 with (−)-α-methylbenzyl isocyanate to form a pair of diasteromeric carbamates represents a published example of synthetic derivatization. These derivatization methods require that the separated carbamates must be chemically reacted to regenerate the optically pure versions of compound 7.

Alternatively, the ability of the imidazoles to form stable salts with common acids can be used to effect ready separation of the enantiomeric mixtures. Diastereomeric acid addition salts can be generated from a variety of enantiomerically pure acids. After separation of the diasteromeric salts by—for example repeated recrystallizations, enantiomerically pure free base compounds can be obtained by adjusting the pH of the aqueous solution to basic and then extracting the desired compound with an organic phase.

METHOD OF USE AND PHARMACEUTICAL COMPOSITION ASPECT

The compounds of this invention have generally been found to be potassium channel activators/openers. Thus their therapeutic effect is where therapeutic intervention involves the enhancement of potassium channel flow.

For their electrophysiological effect the compounds were tested in canine cardiac purkinje fibers in the following manner.

Purkinje fibers are excised from canine cardiac tissue and anchored in a tissue bath and perfused at a rate of 6 mL/min. with modified Tyrode's solution containing the following ions in mmol/L: Na+, 149.8; K+, 4.0; Mg++, 0.5; Ca++, 2.5; Cl−, 134.0; $H_2PO_4$−, 1.8; $HCO_3$−, 24.0; and glucose, 5.5. The solution is gassed with a mixture of 95% oxygen-5% carbon dioxide (pH 7.35-7.40) and maintained at 36°+/−0.5° C. The tissues are stimulated at a control rate of 1.0 Hz through bipolar Teflon-coated platinum electrodes with square wave pulses of 2 msec duration and twice the diastolic threshold current. Intracellular action potentials are recorded with glass microelectrodes (3 M KCl) by using standard recording techniques [*Circ. Res.*, 24, 639 (1969)]. Parameters measured are resting membrane potential, threshold current, action potential amplitude, maximum upstroke velocity, and action potential duration at 50% and 95% (APD95) repolarization. Fibers are stabilized for up to 1 hr. before control measurements are taken. Test compounds are screened in the range of $10^{-8}$ to $10^{-3}$ M concentrations. Data are collected for each compound after 30 min. of exposure to a given concentration.

The compounds are tested for their vascular relaxation effect on the canine coronary artery in the following manner.

The circumflex coronary artery is excised from canine hearts and separated from the adventia. Arteries are cut into approximately 2 mm lengths and placed onto standard holders for use in an aerated muscle bath. The baths are circulated with oxygenated (95% oxygen/5% carbon dioxide) physiological salt solution (PSS) and maintained at 37° C. Coronary arteries are stretched to a tension of 2 gm and then allowed to relax, after which the final tension is equilibrated at 2.5 gm. Repetitive challenges with 20 mM KCl followed by washing and adjustment of the tension is employed to determine the optimum preload conditions for each experiment. When there is no longer an improvement in the KCl response, tissues are relaxed for 30 min. Functional criteria are also assessed by challenging the KCl induced contraction with acetylcholine. Tissues which do not relax at least 65% are not used for testing. Tissues are then washed and allowed to relax for another 30 min.

To test compounds, arteries are precontracted with prostaglandin F2α. When tissues are at a steady state of contraction, compounds are added to the bath cumulatively, beginning at $10^{-8}$ M and increasing to as high as $10^{-4}$ M. After each addition, relaxation is allowed to reach its new plateau before adding the next drug concentration. After the last drug challenge, the artery is rinsed with warm PSS and the process repeated every 10 min. until the tissues are completely relaxed. Function is again checked and tissues that do not respond similarly (within +/−10%) to their pre-drug treatments are not used in the data analysis.

The compounds of the invention as for instance 3,4-dihydro-6-(1H-imidazol-1-yl)-2,2-dimethyl-4-(2-oxo-1-pyrrolidinyl)-2H-benzo[b]pyran-3-ol, trans have been found to be potassium channel activators/openers. Those disease states wherein enhancement of the potassium flow through selected channels would have therapeutic value are the following:

Hypertension; Cardiac Ischemia/Vasospasm and Angina; Cerebral Ischemia/Vasospasm and Stroke; Broncho-constriction/Asthma; Irritable Bladder Syndrome; Impaired Renal Flow/Renal Failure; Congestive Heart Failure; Seizures/Epilepsy; Muscle Spasms; Arrhythmias; Neurodegenerative Diseases; Male Impotence, and Baldness.

The compounds of the invention can be administered orally or parenterally. The dosage and method of administration will be dependent on the age, weight, sex and other characteristics of the subject to be treated and the disease state or states to be treated. The compounds when administered orally or parenterally will be admixed with non-toxic pharmaceutically acceptable carriers, which may be solid or liquid in nature, in accordance with standard pharmaceutical practices taking into account the compound/s to be administered, the dosage form and disease state/s to be effected.

Preparations of the compounds include solid forms as powders, tablets, dispersible granules, capsules, cachets and suppositories. Liquid form preparations include solutions, suspensions and emulsions. Formulations for topical application would include such forms as creams, aerosols, sprays, powders, lotions, ointments and appliques.

The invention described hereinabove is illustrated below in the Preparations and Examples which, however, is not to be construed as limiting the invention.

PREPARATIONS

PREPARATION 1

2,2-DIMETHYL-6-(1H-IMIDAZOL-1-YL)BENZOPYRAN

To a stirred solution of 20 g (0.11 mol) of 6-amino-2,2-dimethylbenzopyran and 70 g (0.91 mol) of ammonium acetate in 190 mL of acetic acid and 770 mL of MeOH at 65° C. is added dropwise over 0.5 h, a mixture of 11.1 g (0.14 mol) of formaldehyde and 20g (0.14 mol) of glyoxal. The mixture is stirred for 1 hour at 65° C., then poured onto 800 g of ice. The pH of the solution is adjusted to 10 by the addition of concentrated ammonium hydroxide. The mixture is extracted with dichloromethane (3×200 mL) and the combined organic extracts are dried with sodium sulfate, filtered and evaporated under reduced pressure. The resulting oil is subjected to chromatography on silica gel utilizing 3% methanol in dichloromethane as eluent. The eluates are analyzed utilizing thin layer chromatography and appropriate fractions are combined and evaporated to produce the title compound.

PREPARATION 2

2,2-DIMETHYL-3,4-EPOXY-6-(1H-IMIDAZOL-1-YL)BENZOPYRAN

Combine the product of Preparation 1 12.0 g (0.053 mol), 48 g (0.265 mol) p-nitroperbenzoic acid, and 3000 mL of dichloromethane and stir for 2 hours at 0° C. Warm the reactants to room temperature and stir an additional 6 hours. The reaction mixture is filtered, then extracted with a 10% aqueous solution of sodium bisulfate (3×500 mL), 10% aqueous sodium bicarbonate (3×500 mL), and water (500 mL). The organic layer is dried with magnesium sulfate, filtered and evaporated to produce the title compound.

PREPARATION 3

TRANS-6-AMINO-3,4-DIHYDRO-2,2-DIMETHYL-4-(2-OXOPYRROLIDIN-1-YL)-2H-1-BENZOPYRAN-3-OL

To a solution of 8.0 g (0.025 mol) of trans-3,4-dihydro-2,2-dimethyl-6-nitro-4-(2-oxopyrrolidin-1-yl)-2H-1-benzopyran-3-ol (U.S. Pat. No. 4,647,670) in 800 mL of ethanol is added 2.8 g of 10% Pd/C, and the reaction mixture is stirred under a hydrogen atmosphere for 18 h. The reaction mixture is filtered, evaporated, and the resulting oil subjected to chromatography on silica gel utilizing 4% methanol in dichloromethane as eluent. The eluates are analyzed by thin layer chromatography, and the appropriate fractions are combined and evaporated to afford the title compound.

EXAMPLES

EXAMPLE 1

3,4-DIHYDRO-6-(1H-IMIDAZOL-1-YL)-2,2-DIMETHYL-4-(2-OXO-1-PYRROLIDINYL)-2H-BENZO[B]PYRAN-3-OL, TRANS

To a stirred solution of 5.0 g (0.018 mol) of the product of Preparation 3 and 12.6 (0.163 g) of ammonium acetate in 150 mL of acetic acid and 600 mL of methanol at 65° C. is added a mixture of 3.4 g (0.024 mol) of glyoxal and 1.9 g (0.24 mol) of formaldehyde dropwise over 1 h. The reaction mixture is allowed to stir an addition 1 h, cooled to room temperature, then treated with a 50% aqueous ammonium hydroxide solution until the pH of the reaction mixture is 10. The reaction mixture is extracted with dichloromethane (7×150 mL). The combined organic extracts are dried with magnesium sulfate, filtered and evaporated under reduced pressure. The residue is subjected to chromatography on silica gel eluting with a mixture of 4% methanol in dichloromethane. The eluates are analyzed by thin layer chromatography, and the appropriate fractions are combined and evaporated to afford the title compound.

$^1$H NMR (DMSO-d$^6$) δ 1.19 (s, 3H), 1.44 (s,3H), 1.98 (m, 2H), 2.40 (m, 2H), 2.99 (m, 1H), 3.36 (m, 1H), 3.73 (m, 1H), 5.01 (d, 1H), 5.64 (d, 1H), 6.98 (d, 1H), 7.01 (m, 1H), 7.07 (s, 1H), 7.40 (m, 1H), 7.58 (s, 1H) and 8.08 (s, 1 H) ppm.

EXAMPLE 2

In a manner similar to the foregoing Preparation and Example and following the methods of schemes A & B, the following compounds may be prepared:

a) 2,2-dimethyl-6-(1H-imidazol-1-yl) -4-(2-oxo- 1-pyrrolidinyl)-2H-benzo[b]pyran.

b) 3,4-dihydro-2,2-dimethyl-6-(1H-imidazol-1-yl)-4-(2-oxo-1-piperidinyl)-2H-benzo[b]pyran-3-ol, trans.

c) 2,2-dimethyl-6-(1H-imidazol-1-yl)-4-(2-oxo-1-piperidinyl)-2H-benzo[b]pyran.

We claim:

1. A compound of the following Formula I:

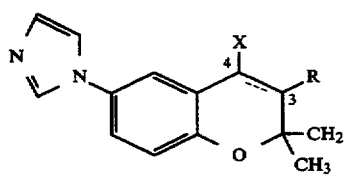

wherein:

R is H or OH;

- - - the dotted line at position 3,4 represents the presence or absence of a double bond, X is 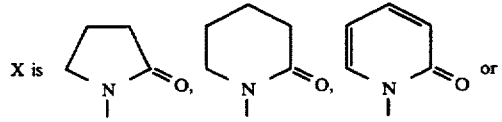

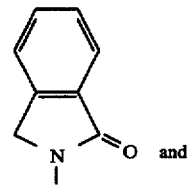

the pharmaceutically acceptable acid addition salts thereof, with the provisos that:

a) R is H when 3,4 is a double bond; and
b) R is OH when 3,4 is a single bond.

2. A compound of claim 1 wherein

X is 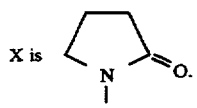

3. A compound of claim 1 wherein

X is 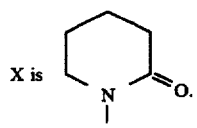

4. A compound of claim 2 which is 3,4-dihydro-6-(1H-imidazol-1-yl)-2,2-dimethyl-4-(2-oxo-1-pyrrolidinyl)-2H-benzo[b]pyran-3-ol, trans.

5. A compound of claim 2 which is 2,2-dimethyl-6-(1H-imidazol-1-yl)-4-(2-oxo-1-pyrrolidinyl)-2H-benzo[b]pyran.

6. A compound of claim 3 which is 3,4-dihydro-2,2-dimethyl-6-(1H-imidazol-1-yl)-4-(2-oxo-1-piperidinyl)-2H-benzo[b]pyran-3-ol, trans.

7. A compound of claim 3 which is 2,2-dimethyl-6-(1H-imidazol-1-yl)-4-(2-oxo-1-piperidinyl)-2H-benzo[b]pyran.

8. A pharmaceutical composition comprising an effective amount of at least one compound according to claim 1, together with one or more nontoxic pharmaceutically acceptable carriers.

* * * * *

UNITED STATES PATENT AND TRADEMARK OFFICE
CERTIFICATE OF CORRECTION

PATENT NO. : 5,416,097
DATED : May 16, 1995
INVENTOR(S) : Paul W. Erhardt, Kenneth J. Shaw It is certified that error appears in the above-identified patent and that said Letters Patent is hereby corrected as shown below:

In the Abstract, item [57]

The following structure:

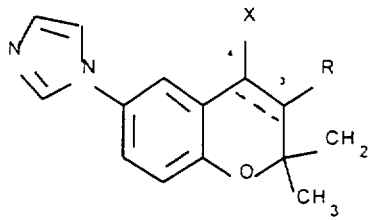   should read   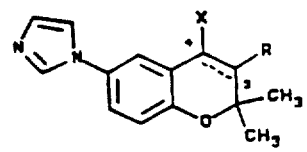

Column 1, line 49

"the provisos that" should read ----- with the provisos that ----- .

Column 3, line 50

"nitro group fin compound 5" should read ----- nitro group in compound 5 ----- .

UNITED STATES PATENT AND TRADEMARK OFFICE
CERTIFICATE OF CORRECTION

PATENT NO. : 5,416,097
DATED : May 16, 1995
INVENTOR(S) : Paul W. Erhardt, Kenneth J. Shaw It is certified that error appears in the above-identified patent and that said Letters Patent is hereby corrected as shown below:

Column 3, line 62

"Scheme A" should read ----- Scheme B ----- .

Column 7, line 55

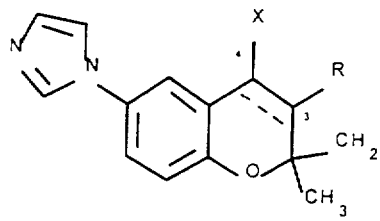   should read   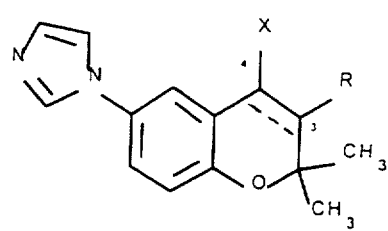

Signed and Sealed this

Thirtieth Day of January, 1996

Attest:

BRUCE LEHMAN

Attesting Officer

Commissioner of Patents and Trademarks